US00PP31295P3

(12) United States Plant Patent
Larse

(10) Patent No.: US PP31,295 P3
(45) Date of Patent: Dec. 31, 2019

(54) STRAWBERRY PLANT NAMED 'OCTAVIA'

(50) Latin Name: ***Fragaria* x *ananassa***
Varietal Denomination: Octavia (a.k.a. '108991'

(71) Applicant: SWEET DARLING SALES, INC., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 15/932,839

(22) Filed: May 4, 2018

(65) Prior Publication Data

US 2018/0324993 P1 Nov. 8, 2018

Related U.S. Application Data

(60) Provisional application No. 62/501,253, filed on May 4, 2017.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Cooley LLP

(57) ABSTRACT

The present invention provides new and distinct strawberry plant designated as 'Octavia' (a.k.a. '108991').

6 Drawing Sheets

Latin name of the genus and species: *Fragaria* x *ananassa*.

Varietal denomination: 'Octavia' (a.k.a. '108991').

BACKGROUND OF THE INVENTION

The present invention relates to new and distinct strawberry plant designated as 'Octavia' (a.k.a. '108991').

'Octavia' (a.k.a. '108991') is the result of a controlled-cross made on Apr. 27, 2012 between a female parent cultivar designated 107967 and a male parent cultivar designated 3236 made by the Inventor and was first fruited in Watsonville, Calif. growing fields. Following selection and during testing, the plant was originally designated '108991' and subsequently named 'Octavia'. 'Octavia' is a day-neutral plant.

This new strawberry plant was asexually reproduced via runners (stolons) by the inventor at Watsonville, Calif. Asexual propagules from the original source have been tested in Watsonville growing fields and to a limited extent, grower fields in high elevation. The properties of this plant were found to be transmissible by such asexual reproduction. The plant is stable and reproduces true to type in successive generations of asexual reproduction.

BRIEF SUMMARY OF THE INVENTION

This invention relates to new and distinctive strawberry plant designated as 'Octavia' (a.k.a. '108991'). The plant is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

'Octavia' has not been observed under all possible environmental conditions, and the phenotype may vary significantly with variations in environment, however with no variance in genotype. The following observations, measurements, and comparisons describe this plant as grown under normal conditions in Watsonville, California unless otherwise noted.

The following traits and photographs in combination distinguish strawberry plant 'Octavia' from known strawberry plants. Plants for the botanical measurements in the present application were grown as annuals. Any color references are made to The Royal Horticultural Society Colour Chart, 1995 Edition, except where general terms of ordinary dictionary significance are used. The plants were 8-month old when the observation was made.

TABLE 1

'Octavia' Characterisitics

| | Characteristic | Description |
|---|---|---|
| General | Plant Habit | perennial |
| | Plant Growth Habit | semi-upright |
| | Day length | neutral |
| | Plant season | Fall |
| | Height (cm) | 39.5 cm |
| | Width (cm) | 35 cm |
| | Density of foliage, vigor | light |
| | Plant vigor | moderate to high |
| | Harvest ease | easy |
| | Rain/weather tolerance | moderate |
| | Crown diameter | 4.0 cm |
| | Fertility | Self-fertile |
| | Freezing quality | moderate |
| Leaf | Terminal leaflet width (mm) | 85.88 mm |
| | Terminal leaflet length (mm) | 78.6 mm |
| | Terminal leaflet length/width ratio | 0.919 |
| | Leaflets per leaf | 3 |
| | Number of leaflets | 120 |

TABLE 1-continued

'Octavia' Characterisitics

| | Characteristic | Description |
|---|---|---|
| | No. teeth/terminal leaflet: | 21 |
| | shape of the terminal leaflet | Orbicular |
| | shape of the terminal leaflet apex | Rounded |
| | shape of the terminal leaflet base | acute |
| | shape of terminal leaflet in cross-section | concave |
| | shape of the terminal leaflet margin | Serrate to crenate |
| | margin description of the terminal | crenate |
| | Color of upper side of leaves | RHS 137A |
| | Color of lower side of leaves | RHS 138D |
| | Terminal Leaflet margin | Flat to revoute |
| | Leaf variegation | absent |
| | Leaf blistering | weak |
| | Leaf glossiness | medium |
| Limbs | Petiole length | 24.5 cm |
| | Petiole diameter | 4.57 mm |
| | Petiole pubescence | medium |
| | Petiole pose of hairs | Horizontal |
| | Petiole color | RHS 145A |
| | Petiolule length | 9.84 mm |
| | Petiolule diameter ( | 2.18 mm |
| | Petiolule color | RHS 145A |
| | Stipule length | 3.5 cm |
| | Stipule width | 11 mm |
| | Stipule pubescence | Medium to dense |
| | Stipule anthocyanin | Present |
| | Stipule color (color code) | RHS 145A |
| | Stipule anthocyanin color | RHS 184D |
| | Pedicel length | 13.5 cm |
| | Pedicel diameter | 2.88 mm |
| | Pedicel color (color code) | RHS 145A |
| | Peduncle length | 19 cm |
| | Peduncle diameter | 3.77 mm |
| | Peduncle color | RHS 145A |
| | Peduncle pubescence | Medium |
| | attitude of hairs on petiole and pedicel | upwards |
| Inflorescence | Inflorescence position relative to foliage | above |
| | Number of flowers | 40 to 56 |
| | Flowers per Truss | 3 to 8 |
| | flower arrangement of petals | free to touching |
| | Flower diameter | 3.3 cm |
| | Petal length | 1.4 cm |
| | Petal width | 1.5 cm |
| | Characteristic | Description |
| | Petal length/width ratio | 0.93 |
| | Petal number per flower | 5 to 6 |
| | Upper petal color | RHS 155C |
| | Lower petal color | RHS 155C |
| | Petal shape | Orbicular to oval |
| | Petal apex | Rounded |
| | Petal margin | entire |
| | Petal base shape | Concave |
| | peduncle size | medium |
| | Calyx diameter | 28.28 mm |
| | Calyx diameter relative to corolla | equal |
| | Inner calyx diameter relative to outer calyx | equal |
| | Corolla diameter | 32.60 mm |
| | Sepal number per flower | 12 |
| | Sepal length | 8.95 mm |
| | Sepal width | 6.11 mm |
| | Sepal shape | elliptical |
| | Sepal apex | convex |
| | Sepal margin | entire |
| | Number of stamen | 27 |
| | Anther color | 12A |
| | Time of flowering (50% of plants in bloom) | April |
| | Shape of stigma | capitate |
| | Color of stigma | 14A |

TABLE 1-continued

'Octavia' Characterisitics

| | Characteristic | Description |
|---|---|---|
| | Length of style | 2.5 mm |
| | Color of style | RHS 12A |
| | Color of the ovary | RHS 145C |
| | Receptacle color | RHS 145A |
| | Number of stamen | 27 |
| | Length of the stamens | 3.9 mm |
| | Shape of anther | dorsifixed |
| | Anther diameter | 0.9 mm |
| | Size of anther | 1.74 mm |
| | Color of anther | RHS 12A |
| | Amount of pollen | scarce to moderate |
| | Color of pollen | RHS 163A |
| | Color of filament | RHS 145C |
| | Length of filament | 3.1 mm |
| Stolon | Stolon length | 62.8 cm |
| | Stolon thickness | Medium to large |
| | Stolon pubescence | Medium |
| | Stolon number | 2 to 5 |
| | Stolon anthocyanin | 181A |
| | Widest diameter of stolon At leaf attachment | 6.17 mm |
| | Stolon color | 145B |
| Fruit | Number of fruit per truss | 2 to 5 |
| | Fruit length (cm) | 4.8 cm |
| | Fruit width (cm) | 4.1 cm |
| | Color of calyx | RHS 145B |
| | Pose of calyx segments | reflexed |
| | Size of calyx in relation to fruit | equal |
| | Fruit length | 4.8 cm |
| | Fruit width | 4.1 cm |
| | Fruit length/width ratio | 1.17 |
| | Fruit skin color | RHS 45A |
| | Fruit flesh color excluding core | RHS 41B |
| | Fruit core color | RHS 39B |
| | Fruit weight (g) | 29 g |
| | Relative fruit size | Medium to large |
| | Predominant fruit shape | long conic |
| | Shape difference between primary & secondary fruits | No shape difference |
| | Width of band without of achenes | medium |
| | Fruit glossiness | strong |
| | Position of achenes in relation to skin surface | below |
| | Achene color | RHS 2C |
| | Achenes per fruit | 475 |
| | Achene weight (g) | 0.28 g |
| | Surface texture | smooth |
| | Texture when tasted | fine |
| | Position of calyx | above |
| | Diameter of calyx | 3.3 cm |
| | level of adherence of calyx | medium |
| | Color of calyx | 145B |
| | Firmness of flesh | firm |
| | Evenness of flesh color | nearly even |
| | Hollow core length | 2.3 cm |
| | Hollow core width | 0.9 cm |
| | Hollow core length/width ratio | 2.56 |
| | Hollow core dize | medium |
| | Type of bearing | Day neutral |
| | Time of fruit ripening | May |
| | Characteristic | Description |
| | Harvest maturity (50% of plants with ripe fruit | June |
| | Appearance Score (1 to 5, with 5 = best) | 4 |
| | Storage longevity | 5 to 11 days |
| | Yield per plant per season | 3.4 kg |
| | Sweetness (Brix) | 7 |
| | Acidity (pH) | 3.44 |

'Octavia' is similar to 'Monterey' (U.S. Plant Pat. No. 19,767), but possesses several distinguishing traits from 'Monterey'. 'Octavia' presents shorter petiole lengths and flower stem lengths than 'Monterey'. 'Monterey' produces mostly conic and long conic fruit while 'Octavia' produces long conic fruit predominantly. The male parent of 'Octavia' differs from 'Octavia' by producing globose fruit. Both the female parent of 'Octavia' and 'Monterey' produce firmer fruit than 'Octavia'. 'Octavia' produces larger strawberries than both of its parents do.

DESCRIPTION OF THE DRAWINGS

The accompanying color photographs depict various characteristics of the cultivars as nearly true as possible to make color reproductions.

Figure 1:
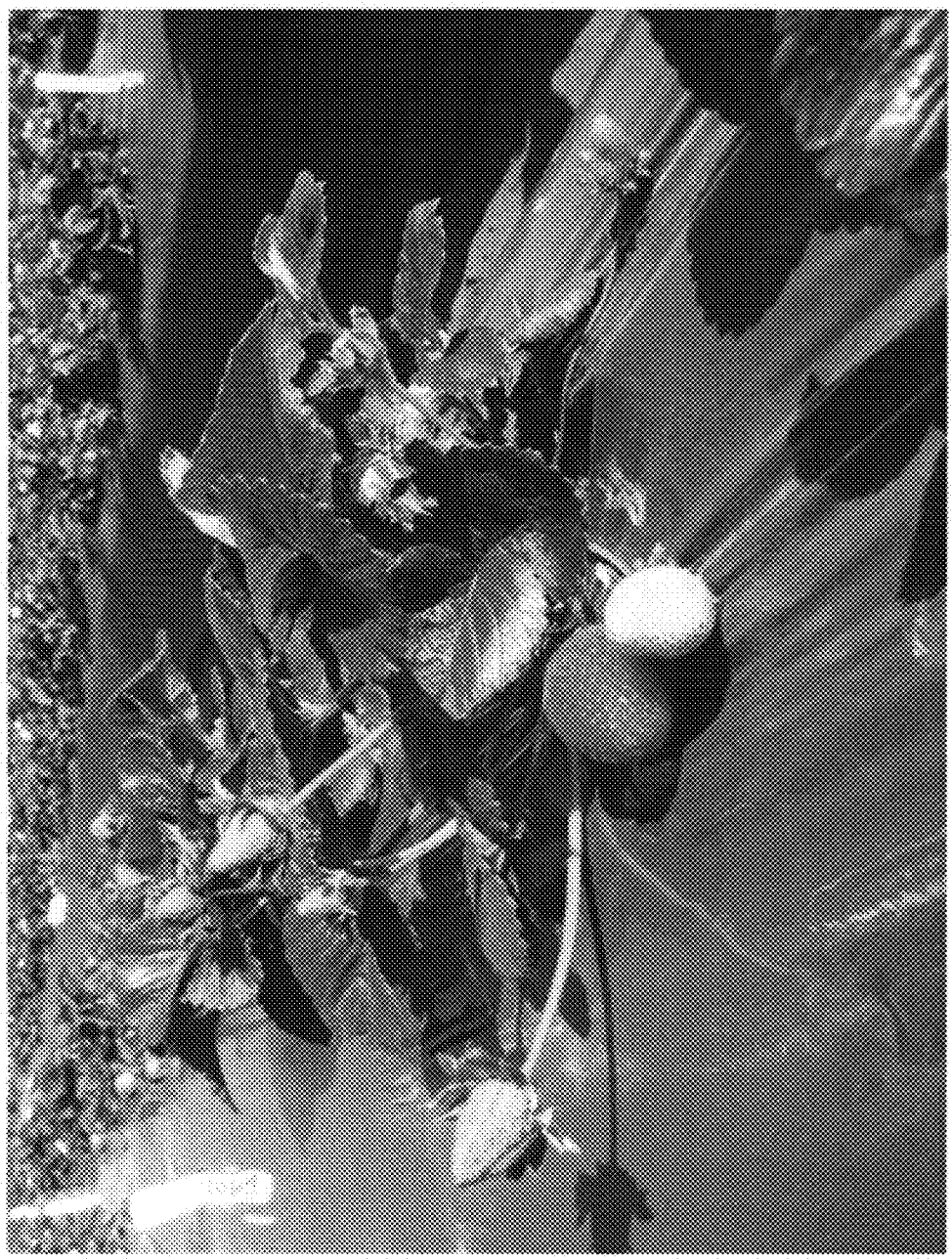
FIG. 1 shows ripe and near-ripe fruits of 'Octavia' about 6-month old.
Figure 2:
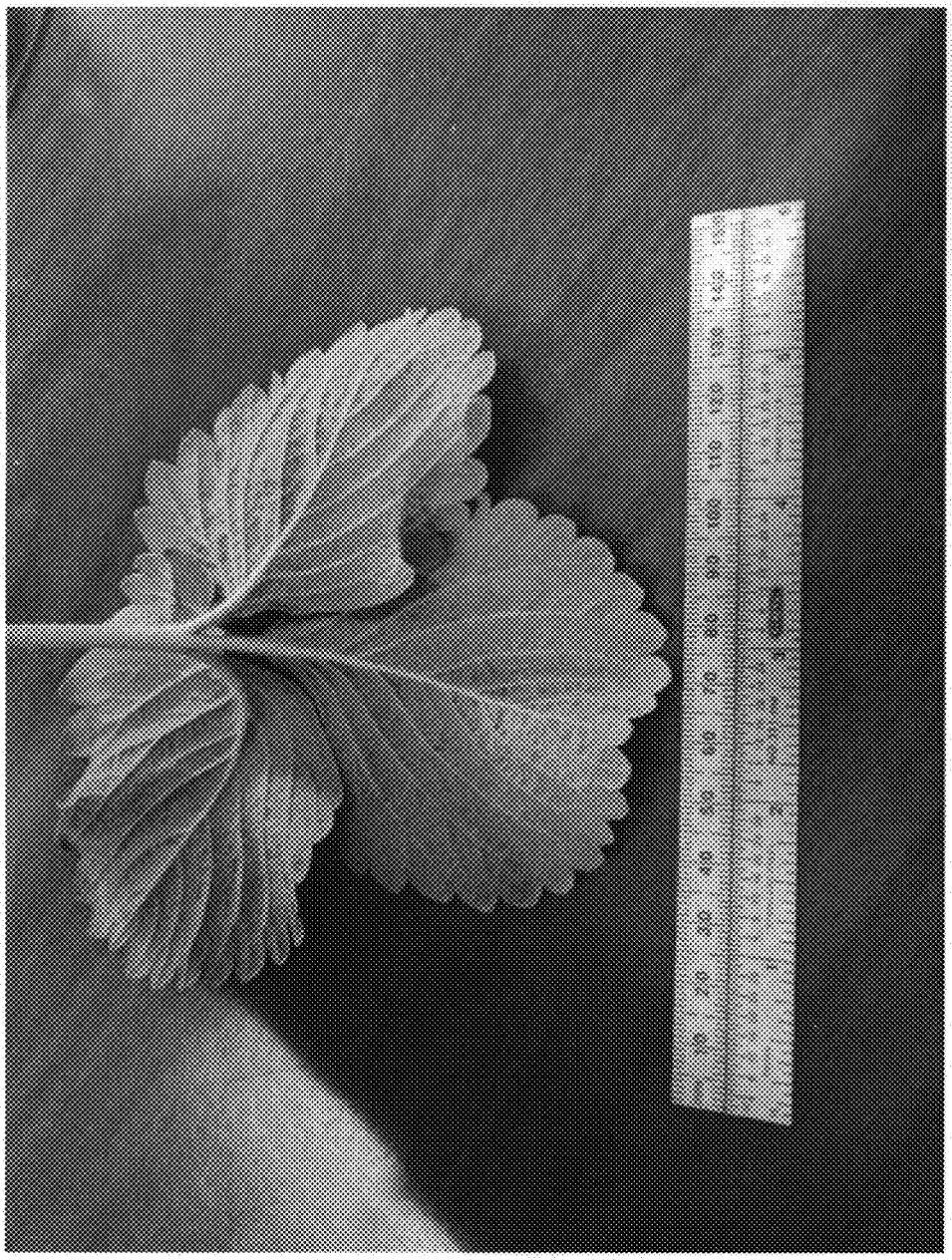
FIG. 2 shows a leaf of 'Octavia' plants.
Figure 3:
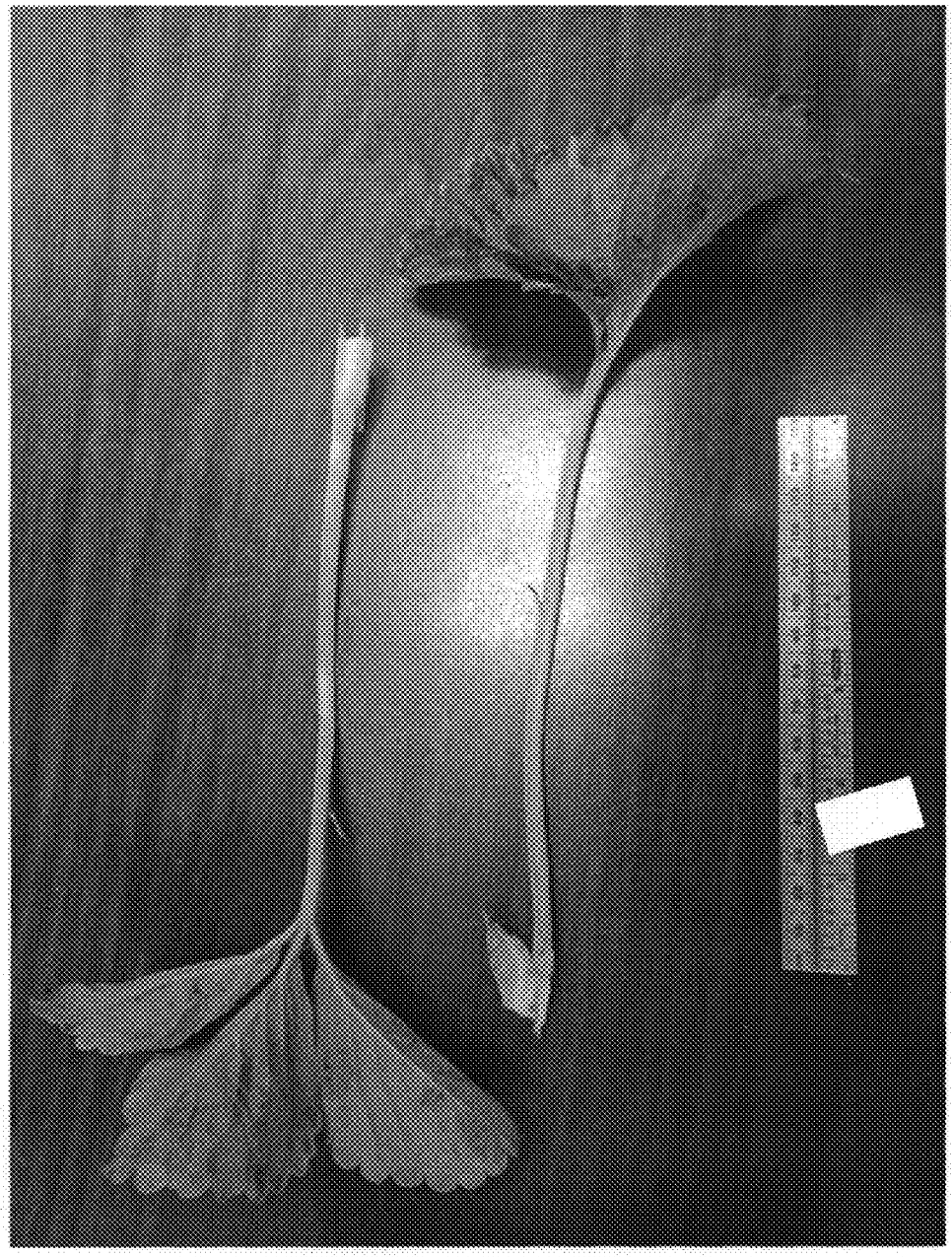
FIG. 3 shows petiole of 'Octavia' plants.
Figure 4:
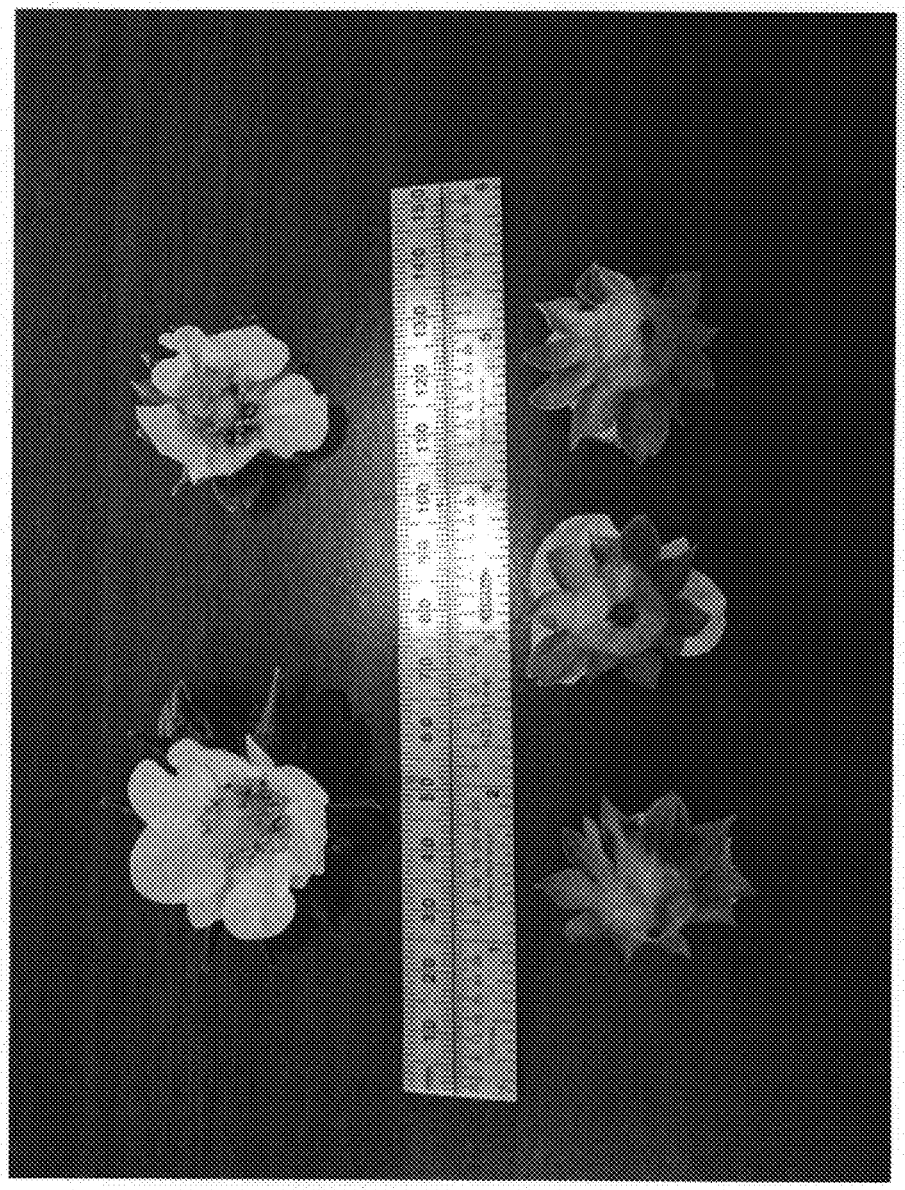
FIG. 4 shows inflorescences of 'Octavia' plants.
Figure 5:
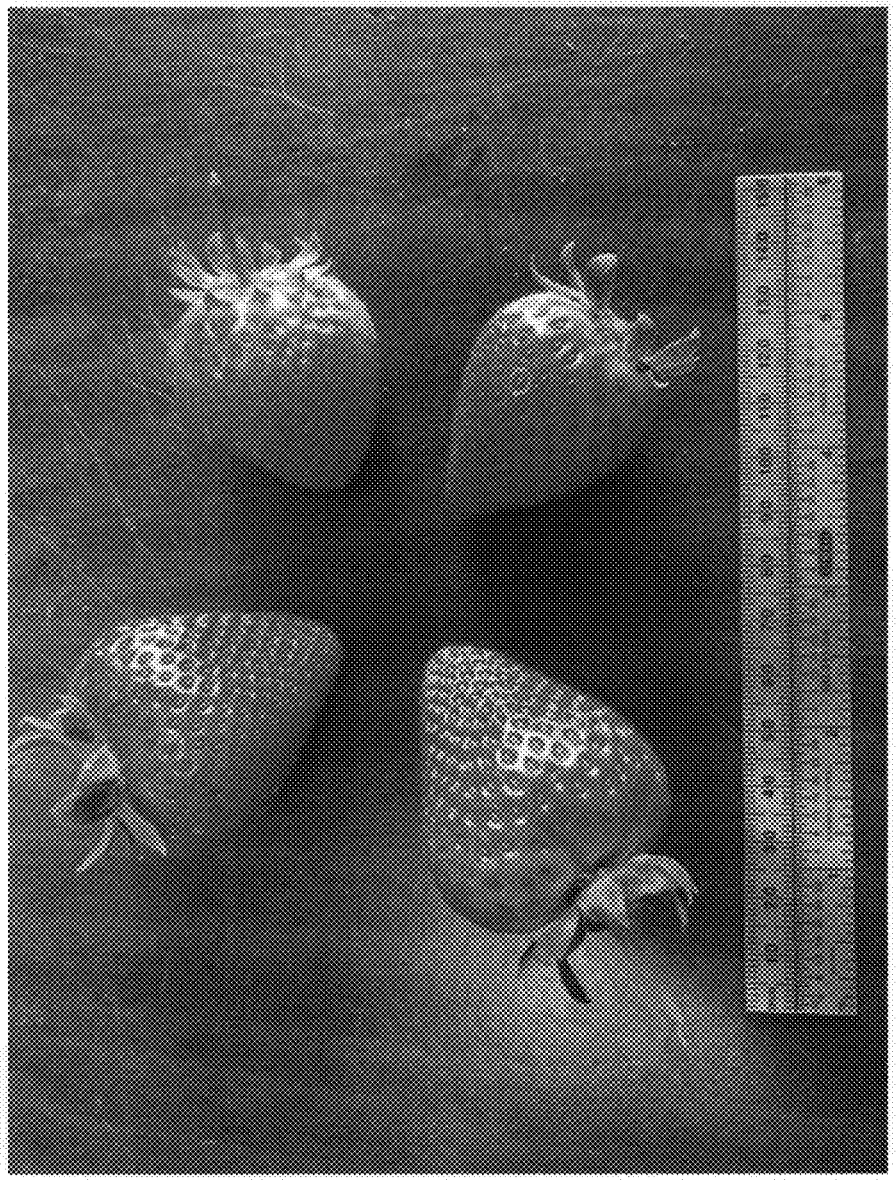
FIG. 5 shows fruits of 'Octavia' plants.
Figure 6:
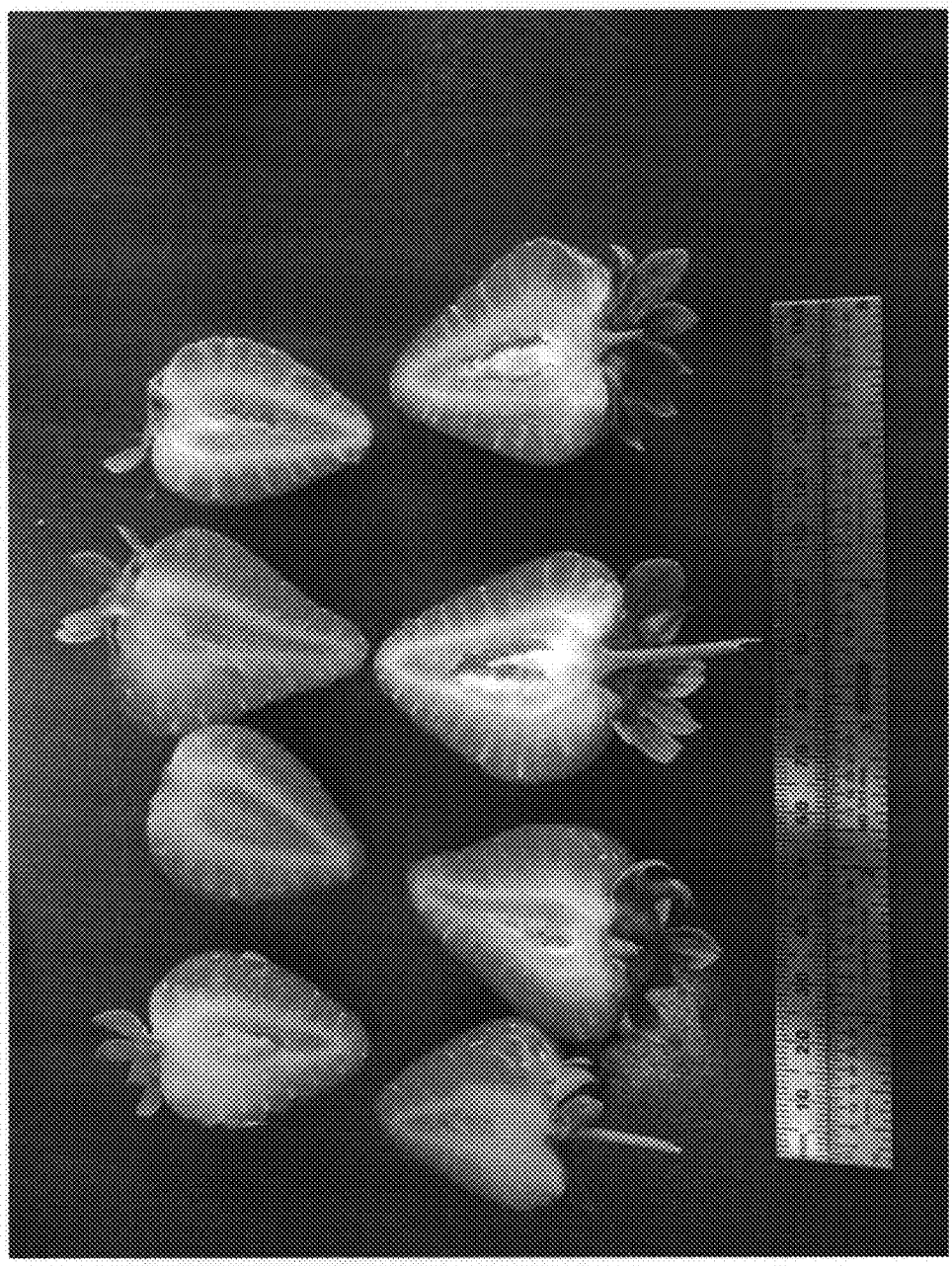
FIG. 6 shows fruits of 'Octavia' plants cut in half.

What is claimed is:

1. A new and distinct cultivar of strawberry plant named 'Octavia', substantially as shown and described herein.

* * * * *